United States Patent [19]

Watkins, Jr.

[11] Patent Number: 5,030,271

[45] Date of Patent: Jul. 9, 1991

[54] SYNERGISTIC HERBICIDAL IMIDAZOLINONE COMPOSITIONS

[75] Inventor: Robert M. Watkins, Jr., Oktibbehha, Miss.

[73] Assignee: American Cyanamid Company, Stamford, Conn.

[21] Appl. No.: 257,478

[22] Filed: Oct. 13, 1988

Related U.S. Application Data

[63] Continuation-in-part of Ser. No. 1,718, Jan. 9, 1987, abandoned.

[51] Int. Cl.$^5$ ............................................. A01N 43/48
[52] U.S. Cl. ......................................................... 71/92
[58] Field of Search ............................................. 71/92

[56] References Cited

U.S. PATENT DOCUMENTS

| | | | |
|---|---|---|---|
| 4,404,012 | 9/1983 | Orwick et al. | 71/92 |
| 4,509,973 | 4/1985 | Kust et al. | 71/92 |
| 4,608,079 | 8/1986 | Los | 71/92 |
| 4,638,068 | 1/1987 | Los | 71/87 |
| 4,647,301 | 3/1987 | Los | 71/92 |

FOREIGN PATENT DOCUMENTS 0041623 12/1981 European Pat. Off. .

Primary Examiner—Glennon H. Hollrah
Assistant Examiner—John D. Pak
Attorney, Agent, or Firm—John W. Hogan, Jr.

[57] ABSTRACT

Synergistic herbicidal imidazolinone compositions, and methods for their use in selective postemergence control of undesirable plant species in the presence of crops; particularly for the selective control of undesirable plant species of the genera: *Ipomoea*, *Sorghum* and *Euphorbia*, in the presence of leguminous crops, by the postemergence application to the foliage of said plants of a novel synergistic combination of an imidazolinyl nicotinic acid, ester or salt with (1) a different imidazolinyl nicotinic acid, ester or salt, (2) an imidazolinyl-3-quinolinecarboxylic acid, ester or salt, or (3) an N-(heterocyclicaminocarbonyl)arylsulfonamide.

16 Claims, No Drawings

SYNERGISTIC HERBICIDAL IMIDAZOLINONE COMPOSITIONS

BACKGROUND OF THE INVENTION

This is a continuation-in- part of U.S. application Ser. No. 001,718 filed on Jan. 9, 1987, now abandoned.

Pitted morningglory, *Ipomea lacunosa;* johnsongrass, *Sorghum halapense;* and spurge, *Euphorbis moculata* are among the most troublesome weeds for farmers in the southeastern United States. Full-season competition, especially of johnsongrass and pitted morningglory, can reduce crop yields (such as soybean yields) significantly resulting in serious economic losses in row crop production. One of the most common practices for controlling johnsongrass and pitted morningglory is the use of post-emergence selective herbicides. However, there is no single selective herbicide currently available which will give effective control of both weed species Substituted imidazolinyl nicotinic and 3-quinolinecarboxylic acids, esters and salts, and their use as herbicidal agents are described in U.S. Pat. Nos. 4,638,068 and 4,647,301 issued to Los and in the counterpart European Patent Specification publication number 0,041,623 A2, published Dec. 16, 1981. These disclosures are primarily concerned with the synthesis of novel substituted imidazolinones and the discovery of the herbicidal activity thereof. The combined use of two or more different imidazolinones is neither suggested nor obvious from these disclosures.

U.S. Pat. No. 4,509,973, issued Apr. 9, 1985, relates to plant growth regulating compositions that contain, as one of the ingredients, a quinolinecarboxylic acid. This patent discloses the treatment of crops with a composition that delivers from 920 to 1610 g/ha of the plant growth regulating agent (2-chloroethyl)trimethylammonium chloride (CCC) as well as about 0.5 to 4 g/ha of 2-(4-isopropyl-4-methyl-5-oxo-2-imidazolin-2-yl) -3-quinolinecarboxylic acid. Kust et al show that composition is effective for increasing crop yields, but do not teach herbicidal activity.

Wherefore, it is an object of this invention to provide synergistic herbicidal imidazolinone compositions and combination treatments for the selective control of undesirable plant species in the presence of leguminous crops.

SUMMARY OF THE INVENTION

This invention relates to synergistic herbicidal imidazolinone compositions and combination treatments effective for the selective control of undesirable plant species in the presence of crops. More particularly, this invention relates to methods and compositions for the selective control of undesirable plant species of the genera: *Ipomoea, Sorghum* and *Euphorbia*, in the presence of leguminous crops, by the postemergence application to the foliage of said plants of a synergistic mixture of an imidazolinyl nicotinic acid, ester or salt, with (1) a different imidazolinyl nicotinic acid, ester or salt, (2) an imidazolinyl-3-quinolinecarboxylic acid, ester or salt, or (3) an N-(heterocyclicaminocarbonyl) arylsulfonamide.

It was surprising to find that the postemergent application of certain (imidazolinyl) nicotinic acids, esters or salts to selected plant species could be synergistically enhanced by the postemergent application of (1) another (imidazolinyl) nicotinic acid, ester or salt; (2) an (imidezolinyl) quinolinecarboxylic acid, ester or salt, or (3) an N-(heterocyclicaminocarbonyl)-arylsulfonamide. It was also surprising to find that while herbicidal effects of such compositions or treatments were enhanced against the undesirable plant species, there was no evidence of enhanced injury to leguminous crops.

DESCRIPTION OF THE INVENTION

In accordance with the present invention, selective synergistic herbicidal compositions are prepared by dissolving or dispersing about 0.05% to 0.20% by volume of a spreader sticker in water and dissolving or dispersing therein a sufficient amount of a formula (I) nicotinic acid, ester or salt, having the structure:

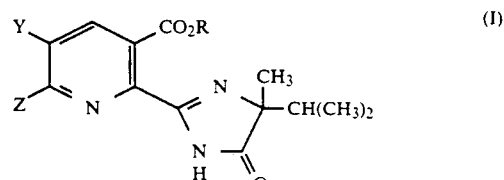

wherein R is H, $C_1$–$C_4$ alkyl, $C_3$–$C_6$ alkenyl, $C_3$–$C_6$ alkynyl, $C_3$–$C_6$ cycloalkyl or a cation; Y and Z each, independently, represent H, $C_1$–$C_4$ alkyl, $C_1$–$C_4$ alkoxy, $C_1$–$C_4$ haloalkyl, $C_1$–$C_4$ haloalkoxy, $C_3$–$C_6$ alkenyl or $C_3$–$C_6$ alkynyl; and except where R is a salt-forming cation, the acid addition salts thereof; to provide the area to be treated with from 0.002 kg/ha to 0.105 kg/ha of said formula (I) nicotinic acid, esters or salt; and a synergistically effective amount of:

(1) a formula II nicotinic or quinolinic acid, ester or salt, having the structure:

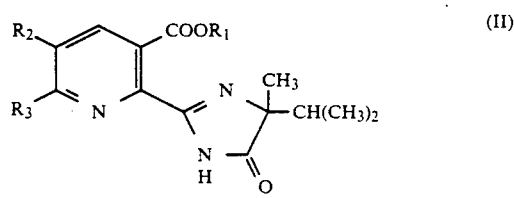

wherein $R_1$ is H, $C_1$–$C_4$ alkyl, $C_3$–$C_6$ alkenyl, $C_3$–$C_6$ alkynyl, $C_3$–$C_6$ cycloalkyl or a cation; $R_2$ and $R_3$ each represent H, $C_1$–$C_4$ alkyl, $C_3$–$C_6$ alkenyl, $C_3$–$C_6$ alkynyl, $C_1$–$C_4$ alkoxy, $C_1$–$C_4$ haloalkyl, $C_1$–$C_4$ haloalkoxy or when $R_2$ and $R_3$ are taken together with the carbons to which they are attached they may form a 5 or 6 membered ring, optionally substituted with one or two halogen, one or two $C_1$–$C_4$ alkyl or one or two $C_1$–$C_4$ alkoxy substituents; and except when $R_1$ is a salt forming cation, the acid addition salts thereof; with the proviso that when formula (II) represents a nicotinic acid, ester or salt, in said composition or combination treatment, at least one of the substituents represented by $R_1$, $R_2$ and $R_3$, in formula II, is different than the substituents represented by R, Y and Z in formula (I); or (2) a formula (III) N-(Heterocyclicaminocarbonyl)arylsulfonamide having the structure:

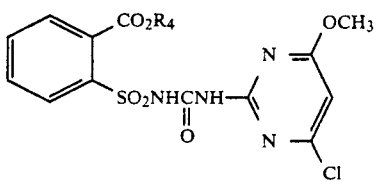
(III)

wherein $R_4$ is $C_2H_5$, $CH(CH_3)_2$ or $CH_2CH=CH_2$; and salts thereof.

When the formula (II) nicotinic acid, ester or salt is used in the above described compositions with a formula (I) nicotinic acid, ester or salt, a sufficient amount of the formula (II) nicotinic acid, ester or salt, is added to the aqueous solution or dispersion to provide the area to be treated with from about 0.002 kg/ha to about 0.105 kg/ha of the formula (II) nicotinic acid, ester or salt. In such compositions formula (I) represents a different nicotinic acid, ester or salt than formula (II).

When formula (II) represents a quinolinecarboxylic acid, ester or salt, in the above described compositions, a sufficient amount of the quinolinecarboxylic acid, ester or salt, is added to the solution or dispersion to provide about 0.070 kg/ha to 0.140 kg/ha thereof to the area of treatment; and when the formula (III) N-(heterocyclicaminocarbonyl) arylsulfonamide is added to the above-said solutions or dispersions, a sufficient amount of the formula (III) sulfonamide is added to provide the treated area with about 0.004 kg/ha to 0.009 kg/ha of said formula (III) sulfonamide.

A spreader sticker is an additive used to better distribution or mix of herbicide (e.g. nonionic surfactants or spreader activators). Among the nonionic surfactants that may be employed in the compositions of the present invention are: sorbitan monolaurate (polysorbate 20) marketed by ICI United States, Inc. as TWEEN 20 ® surfactant; X-77 spreader, a nonionic spreader activator the principal functioning agents of which are alkylarylpolyoxyethylene glycols, free fatty acids and isopropenol marketed by Chevron Chemical Company; ethoxylated nonylphenol; ethoxylated octylphenol; ethoxylated dinonylphenyl, ethoxylated fatty alcohols and octylphenoxy polyethoxyethanol.

In practice, it has been found that the application of aqeuous solutions or dispersions are preferably prepared with about 0.10% to about 0.15% by volume of a nonionic surfactant such as sorbitan monolaurate, a spreader-activator containing an alkylarylpolyoxyethylene, glycol, free fatty acids end isopropanol; or octylphenoxy polyethoxy ethanol.

A preferred method for selectively and synergistically controlling morningglories, johnsongrass and spurge, in the presence of soybeans comprises: applying to the locus in which said soybeans and one or more of the above-said morningglories, johnsongrass or spurge, are growing; a aqueous solution or dispersion containing about 0.10% to 0.15% by volume of a nonionic surfactant as described above; a sufficient amount of a formula (I) herbicide to provide the locus of treatment with about 0.002 to 0.005 kg/ha of isopropylammonium 2-(4-isopropyl-4-methyl-5-oxo-2-imidazolin-2-yl) nicotinate and (a) a sufficient amount of a formula (II) compound to provide said locus of treatment with about 0.070 to 0.140 kg/ha of 2-(4-isopropyl-4-methyl-5-oxo-2-imidazolin-2-yl)-3-quinolinecarboxylic acid; or (b) about 0.018 to 0.105 kg/ha of 5-ethyl-2-(4-isopropyl-4-methyl-5-oxo-2-imidazolin-2-yl)nicotinic acid; or (c) 0.018 to 0.105 kg/ha of 5-methyl-2-(4-isopropyl-4-methyl-5-oxo-2-imidazolin-2-yl)nicotinic acid; or (d) about 0.004 to 0.009 kg/ha of yl)carbamoyl]ethyl ethyl o-{[(((4-chloro-6-methoxy-2-pyrimidinyl)carbamoyl]sulfamoyl}benzoate.

Another preferred method for selectively and synergistically controlling morningglories, Johnsongrass and spurge, in the presence of soybean comprises: applying to the locus in which said soybeans and one or more of the above-said morningglories, johnsongrass or spurge, are growing: an aqueous solution or dispersion containing from 0.10% to 0.15% by volume of a nonionic surfactant as described above and sufficient amounts of a formula (I) nicotinic acid and a formula (II) quinolinecarboxylic acid, to provide said locus of treatment about 0.018 to 0.105 kg/ha of 5-ethyl-2-(4-isopropyl-4-methyl-5-oxo-2-imidazolin-2-yl)nicotinic acid and about 0.070 to 0.014 kg/ha of 2-(4-isopropyl-4-methyl-5-oxo-2-imidazolin-2-yl) -3-quinolinecarboxylic acid.

Another preferred method for controlling morningglory and johnsongrass in the presence of soybeans comprises applying to the locus in which said soybeans and one or more of the above said morningglory and Johnsongrass are growing an aqueous solution or dispersion containing about 0.10% to 0.15% by volume of a nonionic surfactant as described above; a sufficient amount of a formula I herbicide to provide the locus of treatment with about 0.002 to 0.005 kg/ha of isopropylammonium 2-(4-isopropyl-4-methyl-5-oxo-2-imidazolinyl) nicotinate and a sufficient amount of formula II herbicide to provide the locus of treatment with about (a) 0.018 to 0.105 kg/ha of 5-ethyl-2-(4-isopropyl-4-methyl-5-oxo-2-(4-isopropyl--methyl-5-oxo-2-imidazolin -2-yl)nicotinic acid or (b) about 0.070 to 0.140 kg/ha of 2-(4-isopropyl-4-methyl-5-oxo-2-imidazolin-2-yl) -3-quinolinecarboxylic acid.

The compositions of the invention as described above, are applied as postemergence applications to the foliage of undesirable plant species growing in the presence of leguminous crops and to the crops themselves. Since the formula (I) compounds wherein R is hydrogen are acids, they may be readily converted to water soluble acid salts, wherein R is a salt-forming cation, and dissolved or dispersed directly in water and applied as aqueous solutions or suspensions to the crops, the undesirable plant species and the locus of treatment. These aqueous solutions or suspensions will generally also have dispersed or dissolved therein a nonionic surfactant, wetting agent, dispersing agent and/or a spreader-sticker to aid in the application and activity of the compositions applied to the foliage of the undesirable plant species and the crops. The various components of these formulations can be added directly to water or they may be formulated as concentrates, suspensions, emulsions, wettable powders, aqueous flowables or the like and then dispersed in the water prior to application.

The invention is further illustrated by the examples set forth below. These examples are provided only by way of illustration and are not intended as limitations on the invention.

EXAMPLE 1

Evaluation of combination herbicidal treatments for selective control of johnsongrass, spurge and pitted morningglory in the presence of soybeans Major troublesome weeds for southern soybean growers are several different species of morningglories, spurge and johnsongrass.

Thus, for these evaluations, fields having a silty clay soil and a history of heavy infestations of pitted morningglory (*Ipomoea lacunosa*), johnsongrass (*Sorgham halepense*), and spurge (*Euphorbia moculata*) were selected for evaluation of imidazolinone combination treatments. The particular fields were selected because the grower had lost control of these specific weeds using his conventional weed control practices.

The fields were laid out in plots measuring 3.65×9.12 meters. Soybeans (*Glycine max*) were planted in rows arranged on 76 cm centers. Planting was undertaken in mid-May and four weeks after planting the plots were sprayed with 114 liters/hectare of test solution.

All trials were applied using standard accepted weed science procedures. Applications were made with a $CO_2$-powered sprayer. Test design was a replicated complete block design with either three of four replicates. All applications were made post emergence to the weeds and crop.

The compositions evaluated provided the treated area with from 0.18 to 0.105 kg/ha of 5-ethyl-2-(4-isopropy-4-methyl-5-oxo-2-imidazolin -2yl)nicotinic acid plus from 0.070 to 0.14 kg/ha of 2-(4-isopropyl-4-methyl-5-oxo-2-imidazolin-2-yl) -3-quinolinecarboxylic acid; or from 0.070 to 0.14 kg/ha of 2-(4-isopropyl-4-methyl-5-oxo-2-imidazolin-2-yl) -3-quinolinecarboxylic acid plus from 0.002 to 0.005 kg/ha of isopropylammonium 2-(4-isopropyl-4-methyl-5-oxo-2-imidazolin-2-yl) nicotinate; or from 0.018 to 0.105 kg/ha of 5-ethyl-2-(4-isopropyl-4-methyl-5-oxo-2-imidazolin-2-yl) nicotinic acid plus from 0.002 to 0.005 kg/ha of isopropylammonium 2-(4-isopropyl-4-methyl-5-oxo-2-imidazolin-2-yl) nicotinate; or from 0.004 to 0.009 kg/ha of ethyl o-{[(4-chloro-6-methoxy-2-pyrimidinyl) carbamoyl]sulfamoyl)benzoate plus 0.002 to 0.005 kg/ha of isopropylammonium 2-(4-isopropyl-4-methyl-5-oxo-2-imidazolin-2-yl) nicotinate.

The test solutions evaluated were prepared by tank mixing sufficient quantities of aqeuous solutions and/or dispersions of the test compounds and adding to the mixtures thus prepared, a sufficient amount of a non-ionic surfactant such as sorbitan monolaurate (polysorbate 20), i.e. TWEEN 20 ® surfactant, marketed by ICI United States Inc., or a nonionic spreader sticker and activator in which the principal functioning agents are alkylarylpolyoxyethylene, glycols, free fatty acids and isopropanol, marketed as X-77 ® Spreader by Orthro (Chevron Chemical Company), to provide the test solutions with from 0.05 to 0.20% by volume and preferably 0.10 to 0.15% by volume of said nonionic surfactant in the final aqueous solution or suspension applied. In these tests, 0.12% by volume of X-77 ® Spreader was used. Actually among the nonionic emulsifiers which can be employed in the combination treatments of this invention are: ethoxylated nonylphenol, ethoxylated octylphenol, ethoxylated dinonylphenols and ethoxylated fatty alcohols.

The treated plots are examined at intervals during the growing season and rated for percent control of morningglories, johnsongrass and spurge, against the untreated checks. The data reported below is an average of the replicates for that treatment. Crop injury was not evident in these tests.

The combination treatments evaluated in these tests are reported in the tables below. The compounds used in said evaluations are as follows:

Compound A = 5-ethyl-2-(4-isopropyl-4-methyl-5-oxo-2-imidazolin-2-yl) nicotinic acid;

Compound B = 2-(4-isopropyl-4-methyl-5-oxo-2-imidazolin-2-yl) -3-quinolinecarboxylic acid;

C = isopropylammonium 2-(4-isopropyl-4-methyl-5-oxo-2-imidazolin-2-yl) nicotinate; and Compound D = ethyl o-{[4-chloro-6-methoxy-2-pyrimidinyl)carbamoyl]sulfamoyl}benzoate.

TABLE I

| | % Pitted morningglory control 15 days after treatment | | |
|---|---|---|---|
| Product rate kg/ha | Check | Compound B .070 | Compound B .14 |
| Check | 0 | 24.0 | 15.0 |
| Compound A .018 | 8 | *36.0* | *44.0* |
| Compound A .036 | 21 | 41.0 | *44.0* |
| Compound A .070 | 18 | *56.0* | *59.0* |
| Compound A .105 | 58 | 64.0 | 58.0 |

Compound A = 5-ethyl-2-(4-isopropyl-4-methyl-5-oxo-2-imidazo- lin-2-yl)nicotinic acid
Compound B = 2-(4-isopropyl-4-methyl-5-oxo-2-imidazolin-2-yl)- 3-quinolinecarboxylic acid
* = synergistic activity

TABLE II

| | % Pitted morningglory control 29 days after treatment | | |
|---|---|---|---|
| Product rate kg/ha | Check | Compound B .070 | Compound B .14 |
| Check | 0 | 18.0 | 48.0 |
| Compound A .018 | 5.0 | *40.0* | *58.0* |
| Compound A .036 | 23.0 | *70.0* | 66.0 |
| Compound A .070 | 45.0 | *69.0* | 76.0 |
| Compound A .105 | 75.0 | 83.0 | 84.0 |

Compound A = 5-ethyl-2-(4-isopropyl-4-methyl-5-oxo-2-imidazo- lin-2-yl)nicotinic acid
Compound B = 2-(4-isopropyl-4-methyl-5-oxo-2-imidazolin-2-yl)- 3-quinolinecarboxylic acid
* = synergistic activity

TABLE III

| | % Pitted morningglory control 56 days after treatment | | |
|---|---|---|---|
| Product rate kg/ha | Check | Compound B .070 | Compound B .14 |
| Check | 0 | 10.0 | 54.0 |
| Compound A .018 | 8 | *39.0* | *65.0* |
| Compound A .036 | 13 | *75.0* | *69.0* |
| Compound A .070 | 33 | *84.0* | 80.0 |
| Compound A .105 | 80 | 90.0 | 94.0 |

Compound A = 5-ethyl-2-(4-isopropyl-4-methyl-5-oxo-2-imidazo- lin-2-yl)nicotinic acid
Compound B = 2-(4-isopropyl-4-methyl-5-oxo-2-imidazolin-2-yl)- 3-quinolinecarboxylic acid
* = synergistic activity

TABLE IV

% Johnsongrass control 15 days after treatment

| Product rate kg/ha | Check | Compound B .070 | Compound B .14 |
|---|---|---|---|
| Check | 0 | 13.0 | 11.0 |
| Compound A .018 | 11 | 23.0 | *29.0* |
| Compound A .036 | 15 | 19.0 | 25 |
| Compound A .070 | 20 | *35.0* | 28.0 |
| Compound A .105 | 25 | *40.0* | 33.0 |

Compound A = 5-ethyl-2-(4-isopropyl-4-methyl-5-oxo-2-imidazo- lin-2-yl)nicotinic acid
Compound B = 2-(4-isopropyl-4-methyl-5-oxo-2-imidazolin-2-yl)- 3-quinolinecarboxylic acid
* = synergistic activity

TABLE V

% Johnsongrass control 29 days after treatment

| Product rate kg/ha | Check | Compound B .070 | Compound B .14 |
|---|---|---|---|
| Check | 0 | 20.0 | 30.0 |
| Compound A .018 | 5 | *38.0* | *38.0* |
| Compound A .036 | 15 | *53.0* | *48.0* |
| Compound A .070 | 35 | *68.0* | 63.0 |
| Compound A .105 | 63 | 68.0 | 75.0 |

Compound A = 5-ethyl-2-(4-isopropyl-4-methyl-5-oxo-2-imidazo- lin-2-yl)nicotinic acid
Compound B = 2-(4-isopropyl-4-methyl-5-oxo-2-imidazolin-2-yl)- 3-quinolinecarboxylic acid
* = synergistic activity

TABLE VI

% Johnsongrass control 56 days after treatment

| Product rate kg/ha | Check | Compound B .070 | Compound B .14 |
|---|---|---|---|
| Check | 0 | 5.0 | 0.0 |
| Compound A .018 | 5 | 5.0 | 5.0 |
| Compound A .036 | 13 | 13.0 | 10.0 |
| Compound A .070 | 3 | *63.0* | *63.0* |
| Compound A .105 | 54 | *76.0* | *75.0* |

Compound A = 5-ethyl-2-(4-isopropyl-4-methyl-5-oxo-2-imidazo- lin-2-yl)nicotinic acid
Compound B = 2-(4-isopropyl-4-methyl-5-oxo-2-imidazolin-2-yl)- 3-quinolinecarboxylic acid
* = synergistic activity

TABLE VII

% Pitted morningglory control 15 days after treatment

| Product rate kg/ha | Check | Compound C .002 | Compound C .004 |
|---|---|---|---|
| Check | 0 | 4.0 | 16.0 |
| Compound B .070 | 21 | *40.0* | *40.0* |
| Compound B .140 | 34 | 38.0 | 39.0 |
| Compound A .018 | 31 | 31.0 | 30.0 |
| Compound A .036 | 33 | *48.0* | 34.0 |
| Compound A .070 | 41 | 41.0 | 44.0 |
| Compound A .105 | 45 | 45.0 | 51.0 |
| Compound D .004 | 43 | 45.0 | 40.0 |
| Compound D .009 | 45 | 28.0 | 39.0 |

Compound A = 5-ethyl-2-(4-isopropyl-4-methyl-5-oxo-2-imidazo- lin-2-yl)nicotinic acid
Compound B = 2-(4-isopropyl-4-methyl-5-oxo-2-imidazolin-2-yl)- 3-quinolinecarboxylic acid
Compound C = isopropylammonium 2-(4-isopropyl-4-methyl-5- oxo-2-imidazolin-2-yl)nicotinate
Compound D = ethyl o-{[(4-chloro-6-methoxy-2-pyrimidinyl)car- bamoyl]sulfamoyl}benzoate
* = synergistic activity

TABLE VIII

% Pitted morningglory control 29 days after treatment

| Product rate kg/ha | Check | Compound C .002 | Compound C .004 |
|---|---|---|---|
| Check | 0 | 13.0 | 8.0 |
| Compound B .070 | 55 | *71.0* | *78.0* |
| Compound B .140 | 79 | 75.0 | 80.0 |
| Compound A .018 | 28 | *73.0* | *68.0* |
| Compound A .036 | 59 | 65.0 | *76.0* |
| Compound A .070 | 76 | 83.0 | *88.0* |
| Compound A .105 | 81 | 88.0 | *90.0* |
| Compound D .004 | 65 | 78.0 | *80.0* |
| Compound D .009 | 73 | 80.0 | 79.0 |

Compound A = 5-ethyl-2-(4-isopropyl-4-methyl-5-oxo-2-imidazo- lin-2-yl)nicotinic acid
Compound B = 2-(4-isopropyl-4-methyl-5-oxo-2-imidazolin-2-yl)- 3-quinolinecarboxylic acid
Compound C = isopropylammonium 2-(4-isopropyl-4-methyl-5- oxo-2-imidazolin-2-yl)nicotinate
Compound D = ethyl o-{[(4-chloro-6-methoxy-2-pyrimidinyl)car- bamoyl]sulfamoyl}benzoate
* = synergistic activity

TABLE IX

% Pitted morningglory control 56 days after treatment

| Product rate kg/ha | Check | Compound C .002 | Compound C .004 |
|---|---|---|---|
| Check | 0 | 3.0 | 13.0 |
| Compound B .070 | 61 | *68.0* | *76.0* |
| Compound B .140 | 69 | 69.0 | 68.0 |
| Compound A .018 | 25 | *58.0* | *63.0* |
| Compound A .036 | 63 | *73.0* | *78.0* |
| Compound A .070 | 79 | *88.0* | 89.0 |
| Compound A .105 | 86 | *90.0* | 92.0 |
| Compound D .004 | 60 | *78.0* | *75.0* |
| Compound D | 73 | 68.0 | 63.0 |

TABLE IX-continued

% Pitted morningglory control
56 days after treatment

| Product rate kg/ha | Check | Compound C .002 | Compound C .004 |
|---|---|---|---|
| .009 | | | |

Compound A = 5-ethyl-2-(4-isopropyl-4-methyl-5-oxo-2-imidazo- lin-2-yl)nicotinic acid
Compound B = 2-(4-isopropyl-4-methyl-5-oxo-2-imidazolin-2-yl)- 3-quinolinecarboxylic acid
Compound C = isopropylammonium 2-(4-isopropyl-4-methyl-5- oxo-2-imidazolin-2-yl)nicotinate
Compound D = ethyl o-{[(4-chloro-6-methoxy-2-pyrimidinyl)car- bamoyl]sulfamoyl}benzoate
* = synergistic activity

TABLE X

% Johnsongrass control
15 days after treatment

| Product rate kg/ha | Check | Compound C .002 | Compound C .004 |
|---|---|---|---|
| Check | 0 | 8.0 | 13.0 |
| Compound B .070 | 15 | *26.0* | 28.0 |
| Compound B .140 | 26 | 18.0 | 29.0 |
| Compound A .018 | 20 | 25.0 | 21.0 |
| Compound A .036 | 38 | 38.0 | 31.0 |
| Compound A .070 | 44 | 40.0 | 45.0 |
| Compound A .105 | 43 | 45.0 | 46.0 |
| Compound D .004 | 21 | *35.0* | 31.0 |
| Compound D .009 | 35 | 21.0 | 24.0 |

Compound A = 5-ethyl-2-(4-isopropyl-4-methyl-5-oxo-2-imidazo- lin-2-yl)nicotinic acid
Compound B = 2-(4-isopropyl-4-methyl-5-oxo-2-imidazolin-2-yl)- 3-quinolinecarboxylic acid
Compound C = isopropylammonium 2-(4-isopropyl-4-methyl-5- oxo-2-imidazolin-2-yl)nicotinate
Compound D = ethyl o-{[(4-chloro-6-methoxy-2-pyrimidinyl)car- bamoyl]sulfamoyl}benzoate
* = synergistic activity

TABLE XI

% Johnsongrass control
29 days after treatment

| Product rate kg/ha | Check | Compound C .002 | Compound C .004 |
|---|---|---|---|
| Check | 0 | 5.0 | 10.0 |
| Compound B .070 | 10 | *24.0* | 20.0 |
| Compound B .140 | 15 | *23.0* | 23.0 |
| Compound A .018 | 15 | *30.0* | 25.0 |
| Compound A .036 | 35 | *63.0* | 38.0 |
| Compound A .070 | 35 | *60.0* | *73.0* |
| Comound A .105 | 70 | 70.0 | 80.0 |
| Compound D .004 | 23 | 20.0 | 33.0 |
| Compound D .009 | 20 | *28.0* | 25.0 |

Compound A = 5-ethyl-2-(4-isopropyl-4-methyl-5-oxo-2-imidazo- lin-2-yl)nicotinic acid
Compound B = 2-(4-isopropyl-4-methyl-5-oxo-2-imidazolin-2-yl)- 3-quinolinecarboxylic acid
Compound C = isopropylammonium 2-(4-isopropyl-4-methyl-5- oxo-2-imidazolin-2-yl)nicotinate
Compound D = ethyl o-{[(4-chloro-6-methoxy-2-pyrimidinyl)car- bamoyl]sulfamoyl}benzoate
* = synergistic activity

TABLE XII

% Johnsongrass control
56 days after treament

| Product rate kg/ha | Check | Compound C .002 | Compound C .004 |
|---|---|---|---|
| Check | 0 | 0.0 | 0.0 |
| Compound B .070 | 0 | *5.0* | *8.0* |
| Compound B .140 | 5 | 3.0 | 5.0 |
| Compound A .018 | 8 | 5.0 | 5.0 |
| Compound A .036 | 10 | *58.0* | *28.0* |
| Compound A .070 | 40 | *53.0* | *66.0* |
| Compound A .105 | 65 | *66.0* | *83.0* |
| Compound D .004 | 0 | *5.0* | 0.0 |
| Compound D .009 | 3 | *5.0* | *5.0* |

Compound A = 5-ethyl-2-(4-isopropyl-4-methyl-5-oxo-2-imidazo- lin-2-yl)nicotinic acid
Compound B = 2-(4-isopropyl-4-methyl-5-oxo-2-imidazolin-2-yl)- 3-quinolinecarboxylic acid
Compound C = isopropylammonium 2-(4-isopropyl-4-methyl-5- oxo-2-imidazolin-2-yl)nicotinate
Compound D = ethyl o-{[(4-chloro-6-methoxy-2-pyrimidinyl)car- bamoyl]sulfamoyl}benzoate
* = synergistic activity

TABLE XIII

% Upright spurge control
14 days after treatment

| Product rate kg/ha | Check | Compound B 0.280 | Compound B 0.140 | Compound B 0.070 |
|---|---|---|---|---|
| Check | 0 | 33.0 | 20.0 | — |
| Compound A 0.140 | 13.0 | — | *43.0* | — |
| Compound A 0.070 | 37.0 | — | 43.0 | — |
| Compound A 0.036 | 25.0 | — | 40.0 | — |
| Compound C 0.018 | 27.0 | — | *50.0* | — |
| Compound C 0.002 | 0 | — | *37.0* | 33.0 |

Compound A = 5-ethyl-2-(4-isopropyl-4-methyl-5-oxo-2-imidazo- lin-2-yl)nicotinic acid
Compound B = 2-(4-isopropyl-4-methyl-5-oxo-2-imidazolin-2-yl)- 3-quinolinecarboxylic acid
Compound C = isopropylammonium 2-(4-isopropyl-4-methyl-5- oxo-2-imidazolin-2-yl)nicotinate
* = synergistic activity

TABLE XIV

% Upright spurge control
36 days after treatment

| Product rate kg/ha | Check | Compound B 0.280 | Compound B 0.140 | Compound B 0.070 |
|---|---|---|---|---|
| Check | 0 | 30.0 | 37.0 | — |
| Compound A 0.140 | 85.0 | — | 96.0 | — |
| Compound A 0.070 | 87.0 | — | 97.0 | — |
| Compound A 0.036 | 83.0 | — | 94.0 | — |
| Compound C 0.018 | 60.0 | — | 93.0 | — |
| Compound C | 45.0 | — | *90.0* | 95.0 |

TABLE XIV-continued

% Upright spurge control
36 days after treatment

| Product rate kg/ha | Check | Compound B 0.280 | Compound B 0.140 | Compound B 0.070 |
|---|---|---|---|---|
| 0.002 | | | | |

Compound A = 5-ethyl-2-(4-isopropyl-4-methyl-5-oxo-2-imidazo- lin-2-yl)nicotinic acid
Compound B = 2-(4-isopropyl-4-methyl-5-oxo-2-imidazolin-2-yl)- 3-quinolinecarboxylic acid
Compound C = isopropylammonium 2-(4-isopropyl-4-methyl-5- oxo-2-imidazolin-2-yl)nicotinate
* = synergistic activity.

EXAMPLE 2

Evaluation of combination herbicidal treatments for selective control of johnsongrass and pitted morningglory in the presence of soybeans Following essentially the same procedure as hereinabove described in Example 1, further trials were conducted. The following results were obtained and are shown in Table XV and Table XVI below. All values are averaged ratings for % weed control from treatments that were replicated four times. The applications were made at the mid to late postemergence timing stage. Crop tolerance was excellent with no injury from herbicidal compositions noted.

TABLE XV

% Johnsongrass Control
56 Days After Treatment

| Compound rate kg/ha | Check 0.000 | Compound C 0.002 | Compound C 0.004 |
|---|---|---|---|
| Check | 0 | 0 | 0 |
| Compound B 0.070 | 23 | *55* | *55* |
| Compound B 0.140 | 30 | 15 | *60* |
| Compound A 0.018 | 35 | *56* | 20 |
| Compound A 0.036 | 64 | *68* | *95* |
| Compound A 0.070 | 74 | *80* | *83* |
| Compound A 0.105 | 97 | 90 | 95 |
| Compound D 0.004 | 10 | 10 | *13* |
| Compound D 0.008 | 35 | 3 | 10 |

Compound A = 5-ethyl-2-(4-isopropyl-4-methyl-5-oxo-2-imidazo- lin-2-yl)nicotinic acid
Compound B = 2-(4-isopropyl-4-methyl-5-oxo-2-imidazolin-2-yl)- 3-quinolinecarboxylic acid
Compound C = isopropylammonium 2-(4-isopropyl-4-methyl-5- oxo-2-imidazolin-2-yl)nicotinate
Compound D = ethyl o-{[(4-chloro-6-methoxy-2-pyrimidinyl)car- bamoyl]sulfamoyl}benzoate
* = synergistic activity

TABLE XVI

% Pitted Morningglory Control
56 Days After Treatment

| Compound rate kg/ha | Check 0.000 | Compound C 0.002 | Compound C 0.004 |
|---|---|---|---|
| Check | 0 | 0 | 0 |
| Compound B 0.070 | 78 | *92* | *93* |
| Compound B 0.140 | 84 | *90* | *97* |
| Compound A 0.018 | 85 | 80 | *95* |
| Compound A 0.036 | 87 | *90* | 86 |
| Compound A 0.070 | 91 | *94* | *96* |
| Compound A 0.105 | 98 | 93 | 96 |
| Compound D 0.004 | 80 | 79 | *85* |
| Compound D 0.008 | 86 | *88* | 86 |

Compound A = 5-ethyl-2-(4-isopropyl-4-methyl-5-oxo-2-imidazo- lin-2-yl)nicotinic acid
Compound B = 2-(4-isopropyl-4-methyl-5-oxo-2-imidazolin-2-yl)- 3-quinolinecarboxylic acid
Compound C = isopropylammonium 2-(4-isopropyl-4-methyl-5- oxo-2-imidazolin-2-yl)nicotinate
Compound D = ethyl o-{[4-chloro-6-methoxy-2-pyrimidinyl)car- bamoyl]sulfamoyl}benzoate
* = synergistic activity

EXAMPLE 3

Evaluation of combination herbicidal treatments for selective control of pitted morningglory in the presence of soybeans Using essentially the same procedure as hereinabove described for Examples 1 and 2, the effects of the postemergence application of isopropylammonium 2-(4-isopropyl-4-methyl-5-oxo-2-imidazolin-2-yl) nicotinate in combination with 5-ethyl-2(4-isopropyl-4-methyl-5-oxo-2-imidazolin-2-yl)nicotinic acid and the effects of the postemergence application of isopropylammonium 2-(4-isopropyl-4-methyl-5-oxo-2-imidazolin-2-yl) nicotinate in combination with the isopropylamine salt of 2-(4-isopropyl-4-methyl-5-oxo-2-imidazolin-2yl) -3-quinolinecarboxylic acid on pitted morningglory and soybeans in the field were evaluated and recorded below in Tables V and VI. All values are averaged ratings for % morningglory control from treatments that were replicated three times. Crop tolerance was very good with little or no soybean injury evident.

TABLE XVII

% Morningglory Control
14 Days After Treatment

| Compound rate kg/ha | Check 0.000 | Compound C 0.005 |
|---|---|---|
| Control | 0 | 0 |
| Compound B 0.140 | 57 | *78* |
| Compound B 0.035 | 38 | *70* |
| Compound A 0.105 | 72 | *85* |
| Compound A 0.026 | 52 | *72* |

Compound A = 5-ethyl-2-(4-isopropyl-4-methyl-5-oxo-2-imidazo- lin-2-yl)nicotinic acid
Compound B = 2-(4-isopropyl-4-methyl-5-oxo-2-imidazolin-2-yl)- 3-quinolinecarboxylic acid
Compound C = isopropylammonium 2-(4-isopropyl-4-methyl-5- oxo-2-imidazolin-2-yl)nicotinate
* = synergistic activity

TABLE XVIII

% Morningglory Control
28 Days After Treatment

| Compound rate kg/ha | Check 0.000 | Compound C 0.005 |
|---|---|---|
| Control | 0 | 0 |
| Compound B | 80 | *85* |

TABLE XVIII-continued

| | % Morningglory Control 28 Days After Treatment | |
|---|---|---|
| Compound rate kg/ha | Check 0.000 | Compound C 0.005 |
| 0.140 | | |
| Compound B 0.035 | 25 | *72* |
| Compound A 0.105 | 80 | *83* |
| Compound A 0.026 | 23 | *48* |

Compound A = 5-ethyl-2-(4-isopropyl-4-methyl-5-oxo-2-imidazo- lin-2-yl)nicotinic acid
Compound B = 2-(4-isopropyl-4-methyl-5-oxo-2-imidazolin-2-yl)- 3-quinolinecarboxylic acid
Compound C = isopropylammonium 2-(4-isopropyl-4-methyl-5- oxo-2-imidazolin-2-yl)nicotinate
* = synergistic activity

What is claimed is:

1. A method for selectively and synergistically controlling undesirable plant species, selected from the genera consisting of: *Ipomea, Sorghum, Euphorbia*, and combinations thereof which are growing in the presence of one or more leguminous crops, which comprises applying to the locus in which said leguminous crops and one or more of said undesirable plant species are growing a synergistically effective amount of isopropylammonium 2-(4-isopropyl-4-methyl-5-oxo-2-imidazolin-2-yl) nicotinate and 5-ethyl-2-(4-isopropyl-4-methyl-5-oxo-2-imidazolin-2-yl) nicotinic acid at rates of about 0.002 to 0.005 kg/ha of said isopropylammonium 2-(4-isopropyl-4-methyl-5-oxo-2-imidazolin-2-yl) nicotinate and about 0.018 to 0.015 kg/ha of said 5-ethyl-2-(4isopropyl-4-methyl-5-oxo-2-imidazolin-2-yl) nicotinic acid.

2. A method according to claim 1, wherein the undesirable plant species is selected from the group consisting of: morningglories, johnsongrass, spurge and combinations thereof.

3. A method according to claim 2 wherein the leguminous crop is soybeans.

4. A method according to claim 1 wherein the undesirable plant species is selected from the group consisting of: morningglories, johnsongrass, spurge and mixtures thereof, which comprises applying to the locus in which said leguminous crops and one or more of the above-said morningglories, johnsongrass and spurge, are growing; an aqueous composition containing about 0.05% to about 0.20% by volume of a spreader sticker; a sufficient amount of isopropylammonium 2-(4-isopropyl-4-methyl-5-oxo-2-imidazolin-2-yl) nicotinate to provide the locus of treatment with from about 0.002 to about 0.005 kg/ha of said nicotinate and (a) a sufficient amount of 5-ethyl-2-(4-isopropyl-4-methyl-5-oxo-2-imidazolin-2-yl) nicotinic acid to provide from about 0.018 to about 0.105 kg/ha thereof to the locus of treatment.

5. A method according to claim 4 wherein the leguminous crop is soybean.

6. A method according to claim 4 wherein the nonionic surfactant is sorbitan monolaurate (polysorbate 20) and is used in an amount of from about 0.10% to about 0.15% by volume of the aqueous solution used in the application treatment.

7. A method according to claim 4 wherein the spreader sticker is a mixture comprising an alkylarylpolyoxyethylene, one or more glycols, one or more free fatty acids and isopropanol.

8. A method according to claim 1 wherein the undesirable plant species is selected from the group consisting of morningglories, johnsongrass, spurge and combinations thereof and the leguminous crop is soybeans comprising applying to the locus in which said soybeans and one or more of said morningglories, johnsongrass or spurge are growing about 0.002 to about 0.005 kg/ha of isopropylammonium 2-(4-isopropyl-4methyl-5-oxo-2-imidazolin -2-yl)nicotinate and about 0.018 to about 0.070 kg/ha of 5-ethyl-2-(4-isopropyl-4-methyl-5-oxo-2-imidazolin -2-yl)nicotinic acid.

9. A method according to claim 8, wherein the 5-ethyl-2-(4-isopropyl-4-methyl-5-oxo-2-imidazolin-2-yl)nicotinic acid is applied at a rate of about 0.018 kg/ha.

10. A method according to claim 8, wherein the 5-ethyl-2-(4-isopropyl-4-methyl-5-oxo-2-imidazolin-2-yl)nicotinic acid is applied at a rate of about 0.070 kg/ha.

11. A method according to claim 10 wherein the isopropylammonium 2-(4-isopropyl-4-methyl-5-oxo-2-imidazolin-2-yl)nicotinate is applied at a rate of about 0.002 kg/ha.

12. A method according to claim 10 wherein the isopropylammonium 2-(4-isopropyl-4-methyl-5-oxo-2-imidazolin-2-yl)nicotinate is applied at a rate of about 0.004 kg/ha.

13. A method according to claim 3 wherein the isopropylammonium 2-(4- isopropyl-4-methyl-5-oxo-2-imidazolin-2-yl)nicotinate is applied at a rate about 0.004 to 0.005 kg/ha and the 5-ethyl-2-(4-isopropyl-4-methyl-5-oxo-2-imidazolin-2-yl)nicotinic acid is applied at a rate of about 0.105 kg/ha.

14. A method for selectively controlling undesirable plant species selected from the genera consisting of *Ipomea, Sorghum, Euphorbia* and combinations thereof which are growing in the presence of one or more leguminous crops which comprises applying to the locus in which said crops and undesirable plant species are growing about 0.002 to 0.005 kg/ha of isopropylammonium 2-(4-isopropyl-4-methyl-5-oxo-2-imidazolin -2-yl)nicotinate and a synergistically herbicidal effective amount of 5ethyl-2-(4-isopropyl-4-methyl-5-oxo2-imidazolin -2-yl)nicotinic acid.

15. A herbicidal composition for synergistically and selectively controlling undesirable plant species in the presence of leguminous crops comprising a synergistically effective combination of a sufficient amount of isopropylammonium 2-(4-isopropyl-4-methyl-5-oxo-2-imidazolin-2yl)nicotinate to provide about 0.002 to 0.005 kg/ha to said undesirable plant species and a sufficient amount of 5-ethyl-2-(4-isopropyl-4-methyl-5-oxo-2-imidazolin-2-yl)nicotinic acid to provide about 0.018 to 0.105 kg/ha to said undesirable plant species.

16. A herbicidal composition according to claim 15 wherein the leguminous crop is soybeans.

* * * * *

UNITED STATES PATENT AND TRADEMARK OFFICE
CERTIFICATE OF CORRECTION

PATENT NO. : 5,030,271

DATED : 7/9/91

INVENTOR(S) : Robert McCluney Watkins, Jr.

It is certified that error appears in the above-identified patent and that said Letters Patent is hereby corrected as shown below:

Col. 13, line 33, Claim 1, should be corrected to read "...about 0.018 to 0.105 kg/ha...".

Signed and Sealed this

Thirteenth Day of April, 1993

*Attest:*

STEPHEN G. KUNIN

*Attesting Officer*    *Acting Commissioner of Patents and Trademarks*